United States Patent
Dop et al.

(10) Patent No.: US 10,258,559 B2
(45) Date of Patent: Apr. 16, 2019

(54) PREPARATION OF A PULVERULENT/PASTY COMPOSITION COMPRISING A SILICONE ELASTOMER GEL, SOLID PARTICLES AND A BINDER PHASE, AND LIP TREATMENT PROCESS

(71) Applicant: L'OREAL, Paris (FR)

(72) Inventors: Florence Dop, Villiers le Bacle (FR); Alexia Hotton, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/309,078

(22) PCT Filed: Apr. 24, 2015

(86) PCT No.: PCT/FR2015/051124
§ 371 (c)(1),
(2) Date: Nov. 4, 2016

(87) PCT Pub. No.: WO2015/170033
PCT Pub. Date: Nov. 12, 2015

(65) Prior Publication Data
US 2017/0079902 A1    Mar. 23, 2017

(30) Foreign Application Priority Data

May 7, 2014   (FR) ..................................... 14 54104

(51) Int. Cl.
| | | |
|---|---|---|
| *A61K 8/81* | (2006.01) | |
| *A61K 8/891* | (2006.01) | |
| *A61K 8/37* | (2006.01) | |
| *A61Q 1/04* | (2006.01) | |
| *A61Q 1/12* | (2006.01) | |
| *A61K 8/85* | (2006.01) | |
| *A61K 8/895* | (2006.01) | |
| *A61K 8/02* | (2006.01) | |
| *A61K 8/19* | (2006.01) | |
| *A61K 8/34* | (2006.01) | |
| *A61K 8/87* | (2006.01) | |

(52) U.S. Cl.
CPC .............. *A61K 8/891* (2013.01); *A61K 8/022* (2013.01); *A61K 8/19* (2013.01); *A61K 8/345* (2013.01); *A61K 8/37* (2013.01); *A61K 8/375* (2013.01); *A61K 8/8111* (2013.01); *A61K 8/85* (2013.01); *A61K 8/87* (2013.01); *A61K 8/895* (2013.01); *A61Q 1/04* (2013.01); *A61Q 1/12* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 6,235,295 B1 | 5/2001 | Bodelin-Lecomte et al. | |
| 2010/0197805 A1 | 8/2010 | Cassin | |
| 2012/0138078 A1 | 6/2012 | Ricard | |
| 2013/0164235 A1* | 6/2013 | Lebre-Lemonnier | .... A61K 8/31 424/63 |

FOREIGN PATENT DOCUMENTS

| | | |
|---|---|---|
| FR | 2 760 635 A1 | 9/1998 |
| FR | 2 922 104 A1 | 4/2009 |
| FR | 2 945 191 A1 | 11/2010 |
| FR | 2 968 975 A1 | 6/2012 |
| JP | 2005-314369 A | 11/2005 |

OTHER PUBLICATIONS

International Search Report dated Jul. 27, 2015 in PCT/FR2015/051124 filed Apr. 24, 2015.

* cited by examiner

*Primary Examiner* — Jake M Vu
(74) *Attorney, Agent, or Firm* — Oblon, McClelland, Maier & Neustadt, L.L.P.

(57) ABSTRACT

The present invention relates to a process for preparing an anhydrous composition in powder form or in paste form, in which the following steps are performed:

from 30% to 65% by weight, relative to the weight of the composition, of organic, mineral or composite solid particles, and also mixtures thereof, are prepared, 10% to 40% by weight, relative to the weight of the composition, of a mixture comprising at least one organopolysiloxane elastomer conveyed in at least a first silicone or hydrocarbon-based non-volatile oil is prepared, 10% to 45% by weight, relative to the weight of the composition, of an organic binder phase comprising at least a second hydrocarbon-based or silicone non-volatile oil, identical to or different from the first oil, is prepared; at least one pasty compound having a content of between 5% and 25% by weight, relative to the weight of the composition, optionally at least one wax and optionally at least one volatile oil; the wax content not exceeding 5% by weight, relative to the weight of the composition, the binder phase and said conveyed organopolysiloxane elastomer are introduced into the solid particles with stirring; the conveyed organopolysiloxane elastomer being introduced with the binder phase or separately therefrom.

The invention also relates to a process for making up and/or caring for the lips, in which the abovementioned composition is applied.

20 Claims, No Drawings

PREPARATION OF A PULVERULENT/PASTY COMPOSITION COMPRISING A SILICONE ELASTOMER GEL, SOLID PARTICLES AND A BINDER PHASE, AND LIP TREATMENT PROCESS

The present invention relates to a process for preparing a composition in loose or compacted powder form, or in paste form, and also to a process for making up and/or caring for the lips using the same. More particularly, this composition comprises at least one organopolysiloxane elastomer conveyed in at least one first oil, solid particles and a binder phase comprising at least one non-volatile oil and at least one pasty compound.

Cosmetic compositions, in particular care and/or makeup compositions, are in very diverse galenical forms, ranging from the most fluid liquid compositions to solid, pasty or even pulverulent compositions.

In the field of compositions intended to be applied to the lips, they are usually in the form of more or less viscous liquids, especially such as lip glosses, or alternatively in the form of solids, with lipstick wands or alternatively lipsticks in a dish.

Another characteristic of compositions to be applied to the lips is that they make it possible to obtain deposits that have very broad degrees of gloss, since some may be very glossy or, on the contrary, may have a satiny or even matt appearance. The present invention more particularly concerns compositions for obtaining matt deposits.

Compositions intended to be applied to the lips, which are in powder form, are not known on the market at the present time. This type of galenical form is, in fact, more suitable and very widespread for compositions intended to be applied to the skin, such as eyeshadows, blushers or foundations. The major drawback of these pulverulent compositions is that they may be relatively uncomfortable, due to the limited content of non-volatile compounds and/or to the relatively large content of volatile compounds. Although this discomfort is bearable for compositions applied to the skin, it is unacceptable for compositions applied to the lips.

In order to solve this discomfort problem of pulverulent skin or lip makeup compositions, international patent application WO 12/066 457 proposes pulverulent compositions comprising at least 30% by weight of a pulverulent phase containing spherical particles of a crosslinked silicone elastomer, and at least 15% by weight of one or more non-volatile oils.

An improvement in the comfort that is still considered insufficient is observed. The reason for this is that the deposit on the lips is very dry. In addition, the texture of the composition may be granular, very cohesive and quite difficult to take up.

The object of the present invention is thus to provide a solution to the problems mentioned above. In particular, the object of the invention is to propose compositions in powder or paste form that are easy to take up and to apply. These compositions can also be deposited in the form of a thin, homogeneous, matt, comfortable film that shows good persistence.

Thus, one subject of the present invention is a process for preparing an anhydrous composition in powder form or in paste form, in which the following steps are performed:
- from 30% to 65% by weight, relative to the weight of the composition, of organic, mineral or composite solid particles, and also mixtures thereof, are prepared,
- 10% to 40% by weight, relative to the weight of the composition, of a mixture comprising at least one organopolysiloxane elastomer conveyed in at least a first silicone or hydrocarbon-based non-volatile oil is prepared,
- 10% to 45% by weight of an organic binder phase comprising at least a second hydrocarbon-based or silicone non-volatile oil, identical to or different from the first oil, is prepared, at least one pasty compound having a content of between 5% and 25% by weight, relative to the weight of the composition, optionally at least one wax and optionally at least one volatile oil; the wax content not exceeding 5% by weight, relative to the weight of the composition,
- the binder phase and said conveyed organopolysiloxane elastomer are introduced into the solid particles with stirring; the conveyed organopolysiloxane elastomer being introduced with the binder phase or separately therefrom.

Another subject of the invention is a process for making up and/or caring for the lips, in which the composition according to the invention is applied.

The composition according to the invention is homogeneous, stable (at 4° C., 25° C. and 45° C. for at least 2 months) and does not exude oil. Furthermore, it does not have a "waxy" appearance due especially to the presence of pasty compound, which would make the product more difficult to take up. Thus, the texture of the composition remains supple, easy to take up, also easy to spread, with good glidance, as a thin, homogeneous and covering deposit.

The composition obtained according to the invention makes it possible furthermore to obtain very comfortable making-up of the lips which is not tacky and not dry despite the high content in pulverulent phase. It is also significantly matt and has very good persistence of the colour and mattness over time.

Preferably, the composition according to the invention has all of these advantages combined.

It should be noted that, unless otherwise indicated, the limits indicated for a range are included in said range.

The expressions "at least one" and "several" are used without distinction.

The term "anhydrous" especially means that water is preferably not deliberately added to the compositions, but may be present in trace amounts in the various compounds used in the compositions.

The temperatures mentioned later are indicated at atmospheric pressure ($1.013 \times 10^5$ Pa).

Moreover, the solid particles, the mixture of organopolysiloxane elastomer conveyed in a first oil and the binder phase represent 100% by weight of the composition.

The composition according to the invention is in the form of a loose or compacted powder.

A compacted powder more particularly denotes a powder pressed using a manual or mechanical press.

The term "paste" denotes a composition whose hardness cannot be measured according to the "cheese wire" method at 20° C. according to the protocol detailed below, since its hardness is insufficient and does not allow packaging in the form of a wand. Also, the viscosity cannot be measured according to the method that will be described below, since the composition is too viscous.

Protocol for Measuring the Hardness

The composition in wand form is stored at 20° C. for 24 hours before measuring the hardness.

The measurement is performed at 20° C. and consists in transversely cutting a wand of product, which is preferably a circular cylinder, by means of a rigid tungsten wire 250 μm in diameter, by moving the wire relative to the stick at a speed of 100 mm/minute.

The hardness of the samples of compositions of the invention, expressed in $Nm^{-1}$, is measured using a DFGS2 tensile testing machine from the company Indelco-Chatillon.

The measurement is repeated three times and then averaged. The average of the three values read using the tensile testing machine mentioned above, noted Y, is given in grams. This average is converted into newtons and then divided by L which represents the longest distance through which the wire passes. In the case of a cylindrical wand, L is equal to the diameter (in meters).

The hardness is converted into $Nm^{-3}$ by the equation below:

$$(Y \times 10^{-3} \times 9.8)/L$$

Protocol for Measuring the Viscosity:

The viscosity measurement is performed at 25° C., using a Rheomat RM180 viscometer equipped with a No. 4 spindle, the measurement being performed after 10 minutes of rotation of the spindle in the composition (after which time stabilization of the viscosity and of the spin speed of the spindle are observed), at a shear rate of 200 rpm.

The term "physiologically acceptable medium" denotes a medium that is particularly suitable for the application of a composition of the invention to the skin and the lips, and also denotes the aspect in which the composition is packaged.

The present invention and the advantages thereof will emerge more clearly on reading the description and the examples that follow.

Organopolysiloxane Elastomer Conveyed in a First Non-Volatile Oil

As indicated previously, the composition according to the invention comprises at least one organopolysiloxane elastomer (also known as silicone elastomer) conveyed in at least a first silicone or hydrocarbon-based non-volatile oil.

For the purposes of the invention, the term "conveyed" means that the elastomer is brought into the composition in a form predispersed in at least a first oil. More particularly, the elastomer is in the form of a homogeneous mixture of elastomer particles dispersed in the first oil, which is stable for at least 24 hours at 20° C. Preferably, this elastomer is in the form of a gel in at least a first oil. In particular, a powder of silicone elastomer suspended in at least a first oil is not considered, for the purposes of the invention, as an organopolysiloxane elastomer conveyed in at least a first oil.

The term "organopolysiloxane elastomer" or "silicone elastomer" means a soft, deformable organopolysiloxane with viscoelastic properties and especially with the consistency of a sponge or soft sphere. Its modulus of elasticity is such that this material withstands deformation and has a limited capacity for extension and contraction. This material is capable of regaining its original shape after stretching.

It is more particularly a crosslinked silicone elastomer.

In these gels, the organopolysiloxane particles may be spherical or non-spherical particles.

The first silicone or hydrocarbon-based non-volatile oil(s) will be described in detail later.

However, preferably, the organopolysiloxane elastomer used in the composition according to the invention is conveyed in at least a first non-volatile silicone oil chosen especially from non-phenyl silicone oils, from phenyl silicone oils optionally bearing a dimethicone fragment, or mixtures thereof. More advantageously, the first non-volatile oil(s) are chosen from non-phenyl silicone oils, in particular from oils having the INCI name "dimethicone".

The elastomer present in the composition according to the invention may be chosen from non-emulsifying and emulsifying elastomers.

Non-Emulsifying Organopolysiloxane Elastomer

The term "non-emulsifying" defines organopolysiloxane elastomers not containing any hydrophilic chains, and in particular not containing any polyoxyalkylene units (especially polyoxyethylene or polyoxypropylene) or any polyglyceryl units.

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane containing hydroxyl end groups and a diorganopolysiloxane containing at least one hydrogen bonded to silicon, especially in the presence of an organotin; or by crosslinking condensation reaction of a diorganopolysiloxane containing hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst.

In particular, the organopolysiloxane elastomer may be obtained by reaction of a dimethylpolysiloxane with dimethylvinylsiloxy end groups and of methylhydrogenopolysiloxane with trimethylsiloxy end groups, in the presence of a platinum catalyst.

Compound (A) is the base reagent for the formation of organopolysiloxane elastomer, and the crosslinking is performed by addition reaction of compound (A) with compound (B) in the presence of the catalyst (C).

Compound (A) is in particular an organopolysiloxane containing at least two hydrogen atoms bonded to different silicon atoms in each molecule.

Compound (A) may have any molecular structure, in particular a linear-chain or branched-chain structure or a cyclic structure.

Compound (A) may have a viscosity at 25° C. ranging from 1 to 50 000 centistokes, in particular in order to be satisfactorily miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) can thus be chosen from methylhydropolysiloxanes comprising trimethylsiloxy end groups, dimethylsiloxane-methylhydrosiloxane copolymers comprising trimethylsiloxy end groups, and dimethylsiloxane-methylhydrosiloxane cyclic copolymers.

Compound (B) is advantageously a diorganopolysiloxane containing at least two lower alkenyl groups (for example $C_2$-$C_4$); the lower alkenyl group may be chosen from vinyl, allyl and propenyl groups. These lower alkenyl groups may be located at any position on the organopolysiloxane molecule but are preferably located at the ends of the organopolysiloxane molecule. The organopolysiloxane (B) may have a branched-chain, linear-chain, cyclic or network structure but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) can be chosen from methylvinylpolysiloxanes, methylvinylsiloxane-dimethylsiloxane copolymers, dimethylpolysiloxanes comprising dimethylvinylsiloxy end groups, dimethylsiloxane-methylphenylsiloxane copolymers comprising dimethylvinylsiloxy end groups, dimethylsiloxane-diphenylsiloxane-methylvinylsiloxane copolymers comprising dimethylvinylsiloxy end groups, dimethylsiloxane-methylvinylsiloxane copolymers comprising trimethylsiloxy end groups, dimethylsiloxane-methylphenylsiloxane-methylvinylsiloxane copolymers comprising trimethylsiloxy end groups, methyl(3,3,3-trifluoropropyl)polysiloxanes comprising dimethylvinylsiloxy end groups, and dimethylsiloxane-methyl(3,3,3-trifluoropropyl)siloxane copolymers comprising dimethylvinylsiloxy end groups.

In particular, the organopolysiloxane elastomer may be obtained by reaction of a dimethylpolysiloxane with dimethylvinylsiloxy end groups and of methylhydrogenopolysiloxane with trimethylsiloxy end groups, in the presence of a platinum catalyst.

According to another alternative form, compound (B) may be an unsaturated hydrocarbon compound containing at least two lower alkenyl groups (for example $C_2$-$C_4$); the lower alkenyl group may be chosen from vinyl, allyl and propenyl groups. These lower alkenyl groups may be located in any position of the molecule, but are preferably located at the ends. By way of example, mention may be made of hexadiene, in particular of 1,5-hexadiene.

Advantageously, the sum of the number of ethylenic groups per molecule of compound (B) and of the number of hydrogen atoms bonded to silicon atoms per molecule of compound (A) is at least 5.

It is advantageous for compound (A) to be added in an amount such that the molecular ratio of the total amount of hydrogen atoms bonded to silicon atoms in compound (A) to the total amount of all the ethylenically unsaturated groups in compound (B) is within the range from 1.5/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

Catalyst (C) is preferably added in an amount of from 0.1 to 1000 parts by weight and better still from 1 to 100 parts by weight, as clean platinum metal, per 1000 parts by weight of the total amount of compounds (A) and (B).

Spherical non-emulsifying elastomers that may be used include, for example, those sold under the names DC 9040, DC 9041, DC 9509, DC 9505 by the company Dow Corning.

Mention may also be made of those sold under the names KSG-6, KSG-15, KSG-16, KSG-18, KSG-41, KSG-42, KSG-43 and KSG-44 by the company Shin-Etsu; Gransil SR 5CYC Gel, Gransil SR DMF 10 Gel and Gransil SR DC556 Gel from the company Gransil RPS from Grant Industries; 1229-02-167, 1229-02-168 and SFE 839 from the company General Electric.

According to a preferred embodiment, the composition according to the invention comprises, as organopolysiloxane elastomer conveyed in at least a first oil, a non-emulsifying elastomer, preferably spherical, preferably chosen from the compounds sold under the names DC 9040, DC 9041, DC 9509, DC 9505 by the company Dow Corning.

According to one particular embodiment, elastomers may be used as a mixture with a cyclic silicone oil. An example that may be mentioned is the mixture of crosslinked organopolysiloxane/cyclopentasiloxane or a mixture of crosslinked organopolysiloxane/cyclohexasiloxane, for instance Gransil RPS D5 or Gransil RPS D6 from the company Grant Industries.

Emulsifying Organopolysiloxane Elastomer

According to another embodiment, the composition according to the invention comprises, as organopolysiloxane elastomer conveyed in an oil, an emulsifying elastomer.

The term "emulsifying organopolysiloxane elastomer" means an organopolysiloxane elastomer comprising at least one hydrophilic chain, such as polyoxyalkylenated (polyoxyethylenated, polyoxypropylenated) organopolysiloxane elastomers and polyglycerolated silicone elastomers.

The emulsifying organopolysiloxane elastomer may be chosen from polyoxyalkylenated organopolysiloxane elastomers.

The polyoxyalkylenated organopolysiloxane elastomer is a crosslinked organopolysiloxane elastomer that may be obtained by crosslinking addition reaction of diorganopolysiloxane containing at least one hydrogen bonded to silicon and of a polyoxyalkylene containing at least two ethylenically unsaturated groups.

Preferably, the polyoxyalkylenated organopolysiloxane elastomer is obtained by crosslinking addition reaction (A1) of diorganopolysiloxane containing at least two hydrogens each bonded to a silicon, and (B1) of polyoxyalkylene containing at least two ethylenically unsaturated groups, especially in the presence (C1) of a platinum catalyst, as described, for instance, in U.S. Pat. No. 5,236,986 and U.S. Pat. No. 5,412,004.

In particular, the organopolysiloxane may be obtained by reaction of polyoxyalkylene (especially polyoxyethylene and/or polyoxypropylene) with dimethylvinylsiloxy end groups and of methylhydrogenopolysiloxane with trimethylsiloxy end groups, in the presence of a platinum catalyst.

The organic groups bonded to the silicon atoms of compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenylethyl; and substituted monovalent hydrocarbon-based groups such as an epoxy group, a carboxylate ester group or a mercapto group.

Compound (A1) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers, dimethylsiloxane-methylhydrogenosiloxane-laurylmethylsiloxane copolymers containing trimethylsiloxy end groups.

Compound (C1) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

Advantageously, the polyoxyalkylenated organopolysiloxane elastomers may be formed from divinyl compounds, in particular polyoxyalkylenes containing at least two vinyl groups, which react with Si—H bonds of a polysiloxane.

Polyoxyalkylenated elastomers are described especially in U.S. Pat. No. 5,236,986, U.S. Pat. No. 5,412,004, U.S. Pat. No. 5,837,793 and U.S. Pat. No. 5,811,487, the contents of which are incorporated by reference.

Polyoxyalkylenated organopolysiloxane elastomers that may be used include those sold under the names KSG-21, KSG-20, KSG-30, KSG-31, KSG-33, KSG-210, KSG-310, KSG-330 and KSG-340 by the company Shin-Etsu, and DC9010 and DC9011 by the company Dow Corning.

The emulsifying organopolysiloxane elastomer may also be chosen from polyglycerolated organopolysiloxane elastomers.

The polyglycerolated organopolysiloxane elastomer according to the invention is an organopolysiloxane elastomer that may be obtained by crosslinking addition reaction of diorganopolysiloxane containing at least one hydrogen bonded to silicon and of polyglycerolated compounds containing ethylenically unsaturated groups, especially in the presence of a platinum catalyst.

Preferably, the organopolysiloxane elastomer is obtained by crosslinking addition reaction (A2) of diorganopolysiloxane containing at least two hydrogens each bonded to a silicon, and (B2) of glycerolated compounds containing at least two ethylenically unsaturated groups, especially in the presence (C2) of a platinum catalyst.

In particular, the organopolysiloxane may be obtained by reaction of a polyglycerolated compound with dimethylvinylsiloxy end groups and of methylhydrogenopolysiloxane with trimethylsiloxy end groups, in the presence of a platinum catalyst.

Compound (A2) is the base reagent for the formation of an organopolysiloxane elastomer, and the crosslinking is performed by addition reaction of compound (A2) with compound (B2) in the presence of the catalyst (C2).

Compound (A2) is in particular an organopolysiloxane containing at least two hydrogen atoms bonded to different silicon atoms in each molecule.

Compound (A2) may have any molecular structure, especially a linear-chain or branched-chain structure or a cyclic structure.

Compound (A2) may have a viscosity at 25° C. ranging from 1 to 50 000 centistokes, especially so as to be miscible with compound (B2).

The organic groups bonded to the silicon atoms of compound (A2) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Preferably, said organic group is chosen from methyl, phenyl and lauryl groups.

Compound (A2) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers and dimethylsiloxane-methylhydrogenosiloxane-laurylmethylsiloxane copolymers containing trimethylsiloxy end groups.

Compound (B2) may be a polyglycerolated compound corresponding to formula (B') below:

$$C_mH_{2m-1}-O-[Gly]_n-C_mH_{2m-1} \tag{B'}$$

in which m is an integer ranging from 2 to 6, n is an integer ranging from 2 to 200, preferably ranging from 2 to 100, preferably ranging from 2 to 50, preferably ranging from 2 to 20, preferably ranging from 2 to 10 and preferentially ranging from 2 to 5, and in particular n is equal to 3; Gly denotes:

$$-CH_2-CH(OH)-CH_2-O- \text{ or } -CH_2-CH(CH_2OH)-O-$$

Advantageously, the sum of the number of ethylenic groups per molecule in compound (B2) and of the number of hydrogen atoms bonded to silicon atoms per molecule in compound (A2) is at least 4.

It is advantageous for compound (A2) to be added in an amount such that the mole ratio between the total amount of hydrogen atoms bonded to silicon atoms in compound (A2) and the total amount of all the ethylenically unsaturated groups in compound (B2) is within the range from 1/1 to 20/1.

Compound (C2) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C2) is preferably added in an amount of from 0.1 to 1000 parts by weight and better still from 1 to 100 parts by weight, as clean platinum metal, per 1000 parts by weight of the total amount of compounds (A2) and (B2).

The polyglycerolated organopolysiloxane elastomer is conveyed in gel form in at least one hydrocarbon-based oil and/or one silicone oil. In these gels, the polyglycerolated elastomer is often in the form of non-spherical particles.

Polyglycerolated organopolysiloxane elastomers that may be used include those sold under the names KSG-710, KSG-810, KSG-820, KSG-830 and KSG-840 by the company Shin-Etsu.

Preferably, the silicone elastomer conveyed in at least a first oil is non-emulsifying, that is to say free of a hydrophilic chain and in particular free of polyoxyalkylene units and polyglyceryl units.

Advantageously, the organopolysiloxane elastomer under consideration according to the invention is chosen from spherical non-emulsifying organopolysiloxane elastomers.

More particularly, the organopolysiloxane elastomer is obtained by crosslinking addition reaction of diorganopolysiloxane (A) containing at least two hydrogens each bonded to a silicon, and of diorganopolysiloxane (B) containing at least two ethylenically unsaturated groups bonded to silicon, especially in the presence of a platinum catalyst (C).

Advantageously, the composition according to the invention comprises a content of organopolysiloxane elastomer mixture conveyed in at least a first non-volatile oil ranging from 15% to 35% by weight, relative to the weight of the composition.

According to a preferred variant of the present invention, the composition comprises a content of organopolysiloxane elastomer in the composition, expressed as organopolysiloxane elastomer, ranging from 2% to 10% by weight of the composition.

Solid Particles

The composition according to the invention moreover comprises organic, mineral or composite solid particles, and also mixtures thereof.

More particularly, these particles are chosen from coloured solid particles or from fillers, and also mixtures thereof.

Coloured Solid Particles

More particularly, the coloured solid particles are mineral, organic or composite pigments, and also mixtures thereof.

The term "pigments" should be understood as meaning white or coloured, mineral and/or organic particles, which are insoluble in an aqueous solution, and which are intended to colour and/or opacify the composition and/or the deposit produced with the composition.

The pigments may be chosen from monochromatic, in particular inorganic, pigments, organic lakes, nacres, and pigments with an optical effect, for instance reflective pigments and goniochromatic pigments.

The mineral pigments may be chosen from metal oxide pigments, chromium oxides, iron oxides, titanium dioxide, zinc oxides, cerium oxides, zirconium oxides, manganese violet, Prussian blue, ultramarine blue, ferric blue and chromium hydrate, and mixtures thereof.

They may also be pigments having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

Organic lakes are organic pigments formed from a dye attached to a substrate.

They may be chosen, for example, from:
cochineal carmine;
organic pigments of azo dyes, anthraquinone dyes, indigoid dyes, xanthene dyes, pyrene dyes, quinoline dyes, triphenylmethane dyes or fluoran dyes. Among the organic pigments that may in particular be mentioned are those known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6;
insoluble sodium, potassium, calcium, barium, aluminium, zirconium, strontium or titanium salts of acid dyes such as azo, anthraquinone, indigoid, xanthene, pyrene, quinoline, triphenylmethane or fluoran dyes, these dyes possibly comprising at least one carboxylic or sulfonic acid group.

The organic lakes may also be supported on an organic support such as rosin or aluminium benzoate, for example.

Among the organic lakes, mention may be made in particular of those known under the following names: D&C Red No. 2 Aluminium lake, D&C Red No. 3 Aluminium lake, D&C Red No. 4 Aluminium lake, D&C Red No. 6 Aluminium lake, D&C Red No. 6 Barium lake, D&C Red No. 6 Barium/Strontium lake, D&C Red No. 6 Strontium lake, D&C Red No. 6 Potassium lake, D&C Red No. 7 Aluminium lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminium lake, D&C Red No. 9 Barium lake, D&C Red No. 9 Barium/Strontium lake, D&C Red No. 9 Zirconium lake, D&C Red No. 10 Sodium lake, D&C Red No. 19 Aluminium lake, D&C Red No. 19 Barium lake, D&C Red No. 19 Zirconium lake, D&C Red No. 21 Aluminium lake, D&C Red No. 21 Zirconium lake, D&C Red No. 22 Aluminium lake, D&C Red No. 27 Aluminium lake, D&C Red No. 27 Aluminium/Titanium/Zirconium lake, D&C Red No. 27 Barium lake, D&C Red No. 27 Calcium lake, D&C Red No. 27 Zirconium lake, D&C Red No. 28 Aluminium lake, D&C Red No. 30 lake, D&C Red No. 31 Calcium lake, D&C Red No. 33 Aluminium lake, D&C Red No. 34 Calcium lake, D&C Red No. 36 lake, D&C Red No. 40 Aluminium lake, D&C Blue No. 1 Aluminium lake, D&C Green No. 3 Aluminium lake, D&C Orange No. 4 Aluminium lake, D&C Orange No. 5 Aluminium lake, D&C Orange No. 5 Zirconium lake, D&C Orange No. 10 Aluminium lake, D&C Orange No. 17 Barium lake, D&C Yellow No. 5 Aluminium lake, D&C Yellow No. 5 Zirconium lake, D&C Yellow No. 6 Aluminium lake, D&C Yellow No. 7 Zirconium lake, D&C Yellow No. 10 Aluminium lake, FD&C Blue No. 1 Aluminium lake, FD&C Red No. 4 Aluminium lake, FD&C Red No. 40 Aluminium lake, FD&C Yellow No. 5 Aluminium lake, FD&C Yellow No. 6 Aluminium lake.

Mention may also be made of liposoluble dyes, such as, for example, Sudan Red, DC Red 17, DC Green 6, β-carotene, soybean oil, Sudan Brown, DC Yellow 11, DC Violet 2, DC Orange 5 and quinoline yellow.

The chemical substances corresponding to each of the organic dyestuffs cited above are mentioned in the publication "International Cosmetic Ingredient Dictionary and Handbook", 1997 edition, pages 371 to 386 and 524 to 528, published by The Cosmetic, Toiletries and Fragrance Association, the content of which is incorporated into the present patent application by way of reference.

The pigments may also have been subjected to a hydrophobic treatment.

The hydrophobic treatment agent may be chosen from silicones such as methicones, dimethicones and perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups and amino acids; N-acylamino acids or salts thereof; lecithin, isopropyl triisostearyl titanate, and mixtures thereof.

The N-acylamino acids can comprise an acyl group containing from 8 to 22 carbon atoms, such as, for example, a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine.

The term "alkyl" mentioned in the compounds cited above especially denotes an alkyl group containing from 1 to 30 carbon atoms and preferably containing from 5 to 16 carbon atoms.

Hydrophobic-treated pigments are described especially in patent application EP-A-1 086 683.

The dyestuff may also comprise a pigment with a structure that may be, for example, of silica microsphere type containing iron oxide. An example of a pigment having this structure is the product sold by the company Miyoshi under the reference PC Ball PC-LL-100 P, this pigment consisting of silica microspheres containing yellow iron oxide.

For the purposes of the present patent application, the term "nacre" means coloured particles of any form, which may or may not be iridescent, in particular produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, titanium mica coated with an organic dye in particular of the abovementioned type, and also nacreous pigments based on bismuth oxychloride. They may also be mica particles, at the surface of which are superposed at least two successive layers of metal oxides and/or of organic dyestuffs.

The nacres may more particularly have a yellow, pink, red, bronze, orangey, brown, gold and/or coppery colour or tint.

As illustrations of nacres that may be introduced as interference pigments into the first composition, mention may be made of the gold-coloured nacres sold in particular by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold in particular by the company Merck under the name Bronze fine (17384) (Colorona) and Bronze (17353) (Colorona) and by the company Engelhard under the name Super bronze (Cloisonne); the orange nacres sold in particular by the company Engelhard under the name Orange 363C (Cloisonne) and Orange MCR 101 (Cosmica) and by the company Merck under the name Passion orange (Colorona) and Matte orange (17449) (Microna); the brown nacres sold in particular by the company Engelhard under the name Nu-antique copper 340XB (Cloisonne) and Brown CL4509 (Chromalite); the nacres with a copper tint sold in particular by the company Engelhard under the name Copper 340A (Timica); the nacres with a red tint sold in particular by the company Merck under the name Sienna fine (17386) (Colorona); the nacres with a yellow tint sold in particular by the company Engelhard under the name Yellow (4502) (Chromalite); the red nacres with a gold tint sold in particular by the company Engelhard under the name Sunstone G012 (Gemtone); the pink nacres sold in particular by the company Engelhard under the name Tan opale G005 (Gemtone); the black nacres with a gold tint sold in particular by the company Engelhard under the name Nu antique bronze 240 AB (Timica), the blue nacres sold in particular by the company Merck under the name Matte blue (17433) (Microna), the white nacres with a silvery tint sold in particular by the company Merck under the name Xirona Silver, and the golden-green pink-orange nacres sold in particular by the company Merck under the name Indian summer (Xirona), and mixtures thereof.

The cosmetic composition according to the invention may also contain, as coloured particles, at least one material with a specific optical effect.

This effect is different from a simple conventional hue effect, i.e. a unified and stabilized effect as produced by standard coloured particles, for instance monochromatic pigments. For the purposes of the invention, the term "stabilized" means lacking an effect of variability of the colour as a function of the angle of observation or alternatively in response to a temperature change.

For example, this material may be chosen from particles with a metallic glint, goniochromatic colouring agents, diffractive pigments, thermochromic agents, optical brighteners, and also fibres, especially interference fibres. Needless to say, these various materials may be combined so as to afford the simultaneous manifestation of two effects, or even of a novel effect.

Advantageously, the composition according to the invention has a content of coloured particle(s) ranging from 5% to 25% by weight relative to the weight of the composition.

Fillers

The fillers are more particularly organic, mineral or mixed, and may be present alone or as a mixture.

The term "fillers" should be understood as meaning colourless or white solid particles of any form, which are in an insoluble and dispersed form in the medium of the composition, irrespective of the temperature at which the composition is manufactured. These fillers, of mineral or organic nature, make it possible to modify the rheology or texture of the composition, and to give it body or rigidity.

The fillers may be of any form, for example platelet-shaped, spherical, oblong, fibrous, or any other form intermediate between these forms, irrespective of the crystallographic form (for example lamellar, cubic, hexagonal, orthorhombic, etc.).

The fillers according to the invention may or may not be surface-coated, and in particular they may be surface-treated with silicones, amino acids, fluoro derivatives or any other substance that promotes the dispersion and compatibility of the filler in the composition.

Examples of mineral fillers that may be mentioned include talc, mica, fumed or non-fumed silica, which has optionally undergone a hydrophilic or hydrophobic treatment; perlite; kaolin; bentonite; hollow silica microspheres, precipitated calcium carbonate; magnesium carbonate, magnesium hydrocarbonate; hydroxyapatite, boron nitride, glass or ceramic microcapsules; composites of silica and of titanium dioxide, for instance the TSG series sold by Nippon Sheet Glass.

Among the fillers of fumed silica type, which has optionally undergone a hydrophilic or hydrophobic treatment, preferably a hydrophobic treatment, examples that may be mentioned include fillers of the Silica dimethyl silylate type (INCI name according to the CTFA).

The hydrophobic groups may especially be dimethylsilyloxyl or polydimethylsiloxane groups, which are obtained, for example, by treating fumed silica in the presence of polydimethylsiloxane or dimethyldichlorosilane. Silicas thus treated are known as "Silica dimethyl silylate" according to the CTFA (6th edition, 1995). They are sold, for example, under the references Aerosil R972® and Aerosil R974® by the company Degussa and Cab-O-Sil TS-610® and Cab-O-Sil TS-720® by the company Cabot.

Examples of organic fillers that may be mentioned include polyamide powders (Nylon® Orgasol from Atochem), polyethylene powders, polymethyl methacrylate powders, polytetrafluoroethylene (Teflon) powders, acrylic acid copolymer powders (Polytrap from the company Dow Corning), lauroyllysine, hollow polymer microspheres such as those of polyvinylidene chloride/acrylonitrile, for instance Expancel (Nobel Industrie), hexamethylene diisocyanate/trimethylol hexyl lactone copolymer powder (Plastic Powder from Toshiki), silicone resin microbeads (for example Tospearls from Toshiba), synthetic or natural micronized waxes, metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate, Polypore® L 200 (Chemdal Corporation), polyurethane powders, in particular powders of crosslinked polyurethane comprising a copolymer, said copolymer comprising trimethylol hexyl lactone. It may in particular be a hexamethylene diisocyanate/trimethylol hexyl lactone polymer. Such particles are especially commercially available, for example, under the name Plastic Powder D-400® or Plastic Powder D-800® from the company Toshiki, and mixtures thereof.

Organic fillers that may also be mentioned include organopolysiloxane powders other than the polyorganosiloxane elastomer conveyed in at least one first oil described previously. More particularly, mention may be made of powders of crosslinked elastomeric organopolysiloxane coated with silicone resin, especially with silsesquioxane resin, as described, for example, in U.S. Pat. No. 5,538,793.

Such elastomer powders are sold under the names KSP-100®, KSP-101®, KSP-102®, KSP-103®, KSP-104® and KSP-105® by the company Shin-Etsu; mention may also be made of crosslinked organopolysiloxane elastomer powders coated with silicone resin, such as powders of hybrid silicone functionalized with fluoroalkyl groups, sold especially under the name KSP-200 by the company Shin-Etsu; or hybrid silicone powders functionalized with phenyl groups, sold especially under the name KSP-300 by the company Shin-Etsu.

According to a particular embodiment of the invention, the composition comprises a content of organic, mineral or composite filler(s), or mixtures thereof, representing from 10% to 40% by weight, relative to the weight of the composition.

Binder Phase

As indicated previously, the composition according to the invention comprises a binder phase containing at least a second hydrocarbon-based or silicone non-volatile oil, identical to or different from the first oil. Preferably, the second oil(s) are different from the first oil(s).

It should be noted that the first and second hydrocarbon-based or silicone oil(s) are liquid at 25° C. and atmospheric pressure.

It is also pointed out that the hydrocarbon-based or silicone oils are water-immiscible compounds. The term "immiscible" means that the mixture of the same amount of water and of oil does not lead to a homogeneous one-phase solution, at 25° C. and atmospheric pressure.

The term "non-volatile" denotes compounds whose flash point is greater than or equal to 49° C. The flash point is measured in a closed cup using a Pensky-Martens machine.

The description of the non-volatile hydrocarbon-based or silicone oils that follows is suitable both for the first oil(s) and second oil(s).

Hydrocarbon-Based Non-Volatile Oils

As hydrocarbon-based non-volatile oils that are suitable for the purposes of the invention, mention may be made of apolar or polar hydrocarbon-based oils, and also mixtures thereof.

The term "hydrocarbon-based oil" means an oil formed essentially from, or even constituted by, carbon and hydrogen atoms, and possibly oxygen and nitrogen atoms, and not containing any silicon or fluorine atoms.

Apolar Non-Volatile Hydrocarbon-Based Oils

These oils may be of plant, mineral or synthetic origin.

For the purposes of the present invention, the term "apolar oil" means an oil whose solubility parameter at 25° C., $\delta_a$, is equal to 0 $(J/cm^3)^{1/2}$.

The definition and calculation of the solubility parameters in the Hansen three-dimensional solubility space are described in the article by C. M. Hansen: *The three-dimensional solubility parameters*, J. Paint Technol. 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

Preferably, the non-volatile apolar hydrocarbon-based oil may be chosen from linear or branched hydrocarbons of mineral or synthetic origin, such as:

liquid paraffin or derivatives thereof, squalane, isohexadecane, isoeicosane, naphthalene oil, polybutenes, for instance Indopol H-100 (molar mass or MW=965 g/mol), Indopol H-300 (MW=1340 g/mol) and Indopol H-1500 (MW=2160 g/mol) sold or manufactured by the company Amoco, polyisobutenes, hydrogenated polyisobutenes, for instance Parleam® sold by the company Nippon Oil Fats, Panalane H-300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol), or alternatively Parleam Lite sold by NOF Corporation, decene/butene copolymers, polybutene/polyisobutene copolymers, in particular Indopol L-14, polydecenes and hydrogenated polydecenes, for instance: Puresyn 10 (MW=723 g/mol) and Puresyn 150 (MW=9200 g/mol) sold or manufactured by the company Mobil Chemicals, or alternatively Puresyn 6 sold by ExxonMobil Chemical), and mixtures thereof.

Preferably, the non-volatile apolar hydrocarbon-based oil(s), if the composition contains any, are chosen from hydrogenated or non-hydrogenated polybutenes, hydrogenated or non-hydrogenated polyisobutenes and hydrogenated or non-hydrogenated polydecenes, and also mixtures thereof.

Preferably, the composition according to the invention comprises at least one apolar non-volatile hydrocarbon-based oil, in particular those mentioned above.

Polar Hydrocarbon-Based Non-Volatile Oils

These oils are thus formed essentially from, or even consist of, carbon and hydrogen atoms, and optionally comprise one or more oxygen or nitrogen atoms, but do not contain any silicon or fluorine atoms.

They may thus contain alcohol, ester, ether, carboxylic acid, amine and/or amide functions.

Preferably, the polar hydrocarbon-based non-volatile oils are, besides silicon and fluorine, free of heteroatoms such as N and P. The hydrocarbon-based oils are consequently different from silicone oils and fluoro oils.

In the present case, the polar hydrocarbon-based non-volatile oils comprise at least one oxygen atom.

In particular, the polar hydrocarbon-based non-volatile oil(s) comprise at least one alcohol function (it is then an "alcohol oil") or at least one ester function (it is then an "ester oil"). It should be noted that the ester oils may especially be hydroxylated.

The composition may comprise one or more non-volatile hydrocarbon-based oils, in particular chosen from:
- saturated or unsaturated, branched or non-branched $C_{10}$-$C_{26}$, more particularly $C_{10}$-$C_{24}$ and preferably $C_{12}$-$C_{22}$ alcohols, more particularly monoalcohols.

More particularly, the $C_{10}$-$C_{26}$ alcohols are fatty monoalcohols, which are preferably branched when they comprise at least 16 carbon atoms.

As examples of fatty alcohols that may be used according to the invention, mention may be made of linear or branched fatty alcohols, of synthetic origin or alternatively of natural origin, for example alcohols derived from plant material (coconut, palm kernel, palm, etc.) or animal material (tallow, etc.).

Needless to say, other long-chain alcohols may also be used, for instance ether alcohols or alternatively "Guerbet" alcohols.

Finally, use may also be made of certain more or less long fractions of alcohols of natural origin, for instance coconut ($C_{12}$ to $C_{16}$) or tallow ($C_{16}$ to $C_{18}$) or compounds of diol or cholesterol type.

As particular examples of fatty alcohols that may preferably be used, mention may be made especially of lauryl alcohol, isostearyl alcohol, oleyl alcohol, 2-butyloctanol, 2-undecylpentadecanol, 2-hexyldecyl alcohol, isocetyl alcohol and octyldodecanol, and mixtures thereof.

According to one advantageous embodiment of the invention, the alcohol is chosen from octyldodecanol.
- optionally hydroxylated monoesters, diesters or triesters of a $C_2$-$C_8$ monocarboxylic or polycarboxylic acid and of a $C_2$-$C_8$ alcohol.

In particular:
- optionally hydroxylated monoesters of a $C_2$-$C_8$ carboxylic acid and of a $C_2$-$C_8$ alcohol,
- optionally hydroxylated diesters of a $C_2$-$C_8$ dicarboxylic acid and of a $C_2$-$C_8$ alcohol, such as diisopropyl adipate, 2-diethylhexyl adipate, dibutyl adipate or 2-diethylhexyl succinate,
- optionally hydroxylated triesters of a $C_2$-$C_8$ tricarboxylic acid and of a $C_2$-$C_8$ alcohol, such as citric acid esters, such as trioctyl citrate, triethyl citrate, acetyl tributyl citrate, tributyl citrate or acetyl tributyl citrate;
- esters of a $C_2$-$C_8$ polyol of and of one or more $C_2$-$C_8$ carboxylic acids such as glycol diesters of monoacids, such as neopentyl glycol diheptanoate, propylene glycol dioctanoate, or glycerol triesters of monoacids, such as triacetin;
- ester oils, in particular containing at least 18 carbon atoms and even more particularly between 18 and 70 carbon atoms.

Examples that may be mentioned include monoesters, diesters or triesters.

The ester oils may be hydroxylated or non-hydroxylated. Thus, the non-volatile ester oil may be chosen, for example, from:
- monoesters comprising at least 18 carbon atoms and even more particularly comprising between 18 and 40 carbon atoms in total, in particular the monoesters of formula $R_1COOR_2$ in which $R_1$ represents a saturated or unsaturated, linear or branched or aromatic fatty acid residue comprising from 4 to 40 carbon atoms and $R_2$ represents a hydrocarbon-based chain, which is in particular branched, containing from 4 to 40 carbon atoms, on condition that the sum of the carbon atoms of the radicals $R_1$ and $R_2$ is greater than or equal to 18, for instance Purcellin oil (cetostearyl octanoate), isononyl isononanoate, $C_{12}$ to $C_{15}$ alkyl benzoates, 2-ethylhexyl palmitate, octyldodecyl neopentanoate, 2-octyldodecyl stearate, 2-octyldodecyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate or 2-octyldodecyl myristate.

Preferably, they are esters of formula $R_1COOR_2$ in which $R_1$ represents a linear or branched fatty acid residue comprising from 4 to 40 carbon atoms and $R_2$ represents a hydrocarbon-based chain that is in particular branched, containing from 4 to 40 carbon atoms, $R_1$ and $R_2$ being such that the sum of the carbon atoms of the radicals $R_1$ and $R_2$ is greater than or equal to 18.

Even more particularly, the ester comprises between 18 and 40 carbon atoms in total.
- monoesters, in particular containing at least 18 carbon atoms and even more particularly from 18 to 22 carbon atoms, of a fatty acid especially such as lanolic acid, oleic acid, lauric acid or stearic acid, and of diols such as glycols, for instance propylene glycol monoisostearate;
- diesters, especially containing at least 18 carbon atoms and even more particularly comprising between 18 and 60 carbon atoms in total and in particular between 18 and 50 carbon atoms in total. Use may be made especially of diesters of a dicarboxylic acid and of monoalcohols comprising more than 8 carbon atoms, preferably such as diisostearyl malate, diisostearyl adipate; or glycol diesters of monocarboxylic acids, such as neopentyl glycol diheptanoate, diethylene glycol diisononanoate; or polyglyceryl-2 diisostearate (especially such as the compound sold under the commercial reference Dermol DGDIS by the company Akzo);
- hydroxylated monoesters and diesters, preferably with a total carbon number of at least 18 carbon atoms and even more particularly ranging from 18 to 70, for instance polyglyceryl-3 diisostearate, isostearyl lactate, octyl hydroxystearate, octyldodecyl hydroxystearate, diisostearyl malate or glyceryl stearate;
- triesters especially containing at least 35 carbon atoms and even more particularly comprising between 35 and 70 carbon atoms in total, in particular such as triesters of a tricarboxylic acid, such as triisostearyl citrate, or tridecyl trimellitate, or glyceryl triesters of monocarboxylic acids such as polyglyceryl-2 triisostearate;
- tetraesters especially containing at least 35 carbon atoms and even more particularly with a total carbon number ranging from 35 to 70, such as pentaerythritol or polyglycerol tetraesters of a monocarboxylic acid, for instance pentaerythrityl tetrapelargonate, pentaerythrityl tetraisostearate, pentaerythrityl tetraisononanoate, glyceryl tris(2-decyl)tetradecanoate, polyglyceryl-2 tetraisostearate or pentaerythrityl tetrakis(2-decyl)tetradecanoate;
- polyesters obtained by condensation of an unsaturated fatty acid dimer and/or trimer and of diols such as those described in patent application FR 0 853 634. In particular, the unsaturated fatty acid dimer may comprise from 28 to 44 carbon atoms, 2 carboxylic acid functions and 2 to 4 unsaturations; the unsaturated fatty acid trimer may comprise from 42 to 66 carbon atoms, 3 carboxylic acid functions and also 3 to 6 unsaturations. Preferably, use is made of an unsaturated fatty acid dimer, in particular containing 36 carbon atoms and 2 carboxylic acid functions. Mixtures of unsaturated fatty acid dimers and trimers and/or of unsaturated fatty acid (not polymerized, thus corresponding to a monomer) may also be used. Moreover, the diol comprises from 2 to 10 carbon atoms and two hydroxyl functions. In particular, mention may be made of esters of dilinoleic acid and of 1,4-butanediol or propanediol. Mention may especially be made in this respect of the polymer sold by Biosynthis under the name Viscoplast 14436H (INCI name: dilinoleic acid/butanediol copolymer), or else copolymers of polyols and of dimer diacids, and esters thereof, such as Hailucent ISDA;

esters and polyesters of diol dimer and of monocarboxylic or dicarboxylic acid, such as esters of diol dimer and of fatty acid and esters of diol dimer and of dicarboxylic acid dimer, in particular which may be obtained from a dicarboxylic acid dimer derived in particular from the dimerization of an unsaturated fatty acid especially of $C_8$ to $C_{34}$, especially of $C_{12}$ to $C_{22}$, in particular of $C_{16}$ to $C_{20}$ and more particularly of $C_{18}$, such as esters of dilinoleic diacids and of dilinoleic diol dimers, for instance those sold by the company Nippon Fine Chemical under the trade names Lusplan DD-DA5® and DD-DA7®;

polyesters resulting from the esterification of at least one triglyceride of hydroxylated carboxylic acid(s) with an aliphatic monocarboxylic acid and with an aliphatic dicarboxylic acid, which is optionally unsaturated, for instance the succinic acid and isostearic acid castor oil sold under the reference Zenigloss by Zenitech;

hydrocarbon-based plant oils such as fatty acid triglycerides (which are liquid at room temperature), especially of fatty acids containing at least 7 carbon atoms and even more particularly containing from 7 to 40 carbon atoms, such as heptanoic or octanoic acid triglycerides or jojoba oil; mention may be made in particular of saturated triglycerides such as caprylic/capric triglycerides and mixtures thereof, for example such as the product sold under the reference Myritol 318 from Cognis, glyceryl triheptanoate, glyceryl trioctanoate, and $C_{18-36}$ acid triglycerides such as those sold under the reference Dub TGI 24 by Stéarineries Dubois, and unsaturated triglycerides such as castor oil, olive oil, ximenia oil or pracaxi oil;

vinylpyrrolidone/1-hexadecene copolymers, for instance the product sold under the name Antaron V-216 (also known as Ganex V216) by the company ISP (MW=7300 g/mol), $C_{12}$-$C_{26}$ fatty acids, preferably $C_{12}$-$C_{22}$ fatty acids, which are preferably unsaturated, such as oleic acid, linoleic acid or linolenic acid, and mixtures thereof;

dialkyl carbonates, the 2 alkyl chains possibly being identical or different, such as dicaprylyl carbonate sold under the name Cetiol CC® by Cognis;

and mixtures thereof.

Preferably, the non-volatile polar hydrocarbon-based oil(s), if the composition contains any, are chosen from ester oils, and in particular hydroxylated or non-hydroxylated monoesters and diesters, comprising at least 18 carbon atoms in total, and also mixtures thereof.

Preferably, the composition according to the invention comprises at least one polar non-volatile oil, advantageously chosen from those mentioned above.

Non-Volatile Silicone Oils

According to one variant of the invention, the binder phase comprises at least one non-volatile silicone compound that is liquid at 25° C. and atmospheric pressure, chosen from non-phenyl silicone oils, from phenyl silicone oils optionally bearing a dimethicone fragment, or mixtures thereof, which are identical to or different from the first non-volatile silicone oil(s).

Non-Volatile Non-Phenyl Silicone Oils

The term "non-phenylated silicone oil" or "non-phenyl silicone oil" denotes a silicone oil which does not bear any phenyl substituents.

Representative examples of these non-volatile non-phenyl silicone oils which may be mentioned include polydimethylsiloxanes; alkyl dimethicones; vinylmethyl methicones; and also silicones modified with aliphatic groups and/or with functional groups such as hydroxyl, thiol and/or amine groups.

It should be noted that "dimethicone" (INCI name) corresponds to a polydimethylsiloxane (chemical name).

In particular, these oils may be chosen from the following non-volatile non-phenyl silicone oils:

polydimethylsiloxanes (PDMSs),

PDMSs comprising aliphatic groups, in particular alkyl or alkoxy, which are pendent and/or at the end of the silicone chain; these groups each comprising from 2 to 24 carbon atoms. An example that may be mentioned is cetyl dimethicone sold under the commercial reference Abil Wax 9801 from Evonik Goldschmidt, PDMSs comprising at least one aliphatic group and/or at least one functional group such as hydroxyl, thiol and/or amine groups, polysiloxanes modified with fatty acids, fatty alcohols or polyoxyalkylenes, and mixtures thereof, cyclic silicones, for instance octamethylcyclotetrasiloxane, dodecamethylcyclohexasiloxane or cyclopentasiloxane.

The non-volatile non-phenyl silicone oil is preferably chosen from non-volatile dimethicone oils.

Preferably, these non-volatile non-phenylated silicone oils are chosen from polydimethylsiloxanes; alkyl dimethicones and also PDMSs comprising at least one aliphatic group, in particular $C_2$-$C_{24}$ alkyl groups and/or at least one functional group such as hydroxyl, thiol and/or amine groups.

The non-phenylated silicone oil may be chosen in particular from silicones of formula (I'):

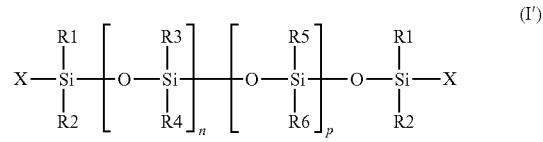

in which:

$R_1$, $R_2$, $R_5$ and $R_6$ are, together or separately, an alkyl radical containing from 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound, in particular whose viscosity at 25° C. is between 2 centistokes (cSt) and 800 000 cSt.

As non-volatile non-phenyl silicone oils which can be used according to the invention, mention may be made of those for which:
- the substituents $R_1$ to $R_6$ and X represent a methyl group, and p and n are such that the viscosity is 500 000 cSt (i.e. 450 000 mPa·s), for example the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt (i.e. 450 000 mPa·s) by the company Dow Corning,
- the substituents $R_1$ to $R_6$ and X represent a methyl group, and p and n are such that the viscosity is 60 000 cSt (54 000 mPa·s), for example the product sold under the name Dow Corning 200 Fluid 60 000 CS by the company Dow Corning, and the product sold under the name Wacker Belsil DM 60 000 by the company Wacker,
- the substituents $R_1$ to $R_6$ and X represent a methyl group, and p and n are such that the viscosity is 100 cSt (i.e. 90 mPa·s) or 350 cSt (i.e. 315 mPa·s), for example the products sold respectively under the names Belsil DM100 and Dow Corning 200 Fluid 350 CS by the company Dow Corning,
- the substituents $R_1$ to $R_6$ represent a methyl group, the group X represents a hydroxyl group, and n and p are such that the viscosity is 700 cSt (630 mPa·s), for example the product sold under the name Baysilone Fluid T0.7 by the company Momentive.
- the substituents $R_1$ to $R_5$ and X represent a methyl group, and p and n are such that the viscosity is 5 cSt, for example the product sold under the name Xiameter® PMX-200 Silicone Fluid 5 CS by Dow Corning.

Dodecamethylpentasiloxane and decamethyltetrasiloxane are also suitable for use.

Non-Volatile Phenyl Silicone Oils

The expression "phenylated silicone oil" or "phenyl silicone oil" denotes a silicone oil bearing at least one phenyl substituent.

These phenyl silicone oils may be chosen from those which also bear at least one dimethicone fragment, or from those which do not bear one.

According to the invention, a dimethicone fragment corresponds to the following unit:

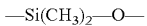
—Si(CH$_3$)$_2$—O—

The non-volatile phenyl silicone oil may thus be chosen from:
a) phenyl silicone oils optionally bearing a dimethicone fragment corresponding to the following formula (I):

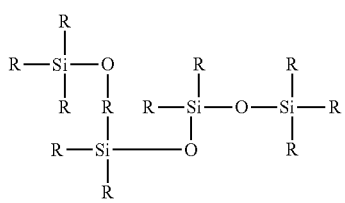
(I)

in which the groups R, which are monovalent or divalent, represent, independently of each other, a methyl or a phenyl, with the proviso that at least one group R represents a phenyl.

Preferably, in this formula, the phenyl silicone oil comprises at least three, for example at least four, at least five or at least six, phenyl groups.

b) phenyl silicone oils optionally bearing a dimethicone fragment corresponding to formula (II) below:

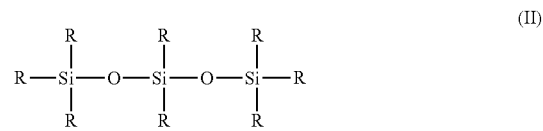
(II)

in which the groups R represent, independently of each other, a methyl or a phenyl, with the proviso that at least one group R represents a phenyl.

Preferably, in this formula, the compound of formula (II) comprises at least three, for example at least four or at least five, phenyl groups.

Mixtures of different phenylorganopolysiloxane compounds described above can be used.

Examples that may be mentioned include mixtures of triphenyl-, tetraphenyl- or pentaphenyl-organopolysiloxanes.

Among the compounds of formula (II), mention may more particularly be made of phenyl silicone oils which do not bear a dimethicone fragment, corresponding to formula (II) in which at least 4 or at least 5 radicals R represent a phenyl radical, the remaining radicals representing methyls.

Such non-volatile phenyl silicone oils are preferably trimethylpentaphenyltrisiloxane or tetramethyltetraphenyltrisiloxane. They are in particular sold by Dow Corning under the reference PH-1555 HRI or Dow Corning 555 Cosmetic Fluid (chemical name: 1,3,5-trimethyl-1,1,3,5,5-pentaphenyltrisiloxane; INCI name: trimethylpentaphenyltrisiloxane), or the tetramethyltetraphenyltrisiloxane sold under the reference Dow Corning 554 Cosmetic Fluid by Dow Corning may also be used.

They correspond especially to formulae (III) and (III') below:

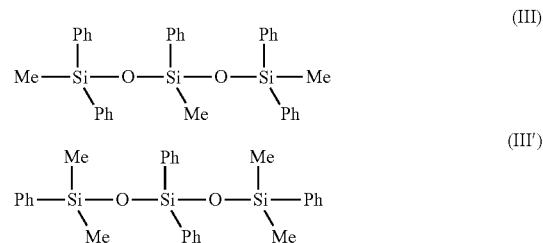

in which Me represents methyl, and Ph represents phenyl.

c) phenyl silicone oils bearing at least one dimethicone fragment corresponding to formula (IV) below:

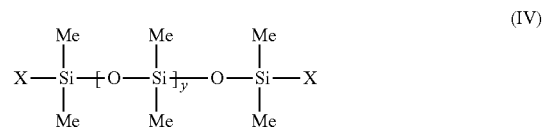
(IV)

in which Me represents methyl, y is between 1 and 1000 and X represents —CH$_2$—CH(CH$_3$)(Ph).

d) phenyl silicone oils corresponding to formula (V) below, and mixtures thereof:

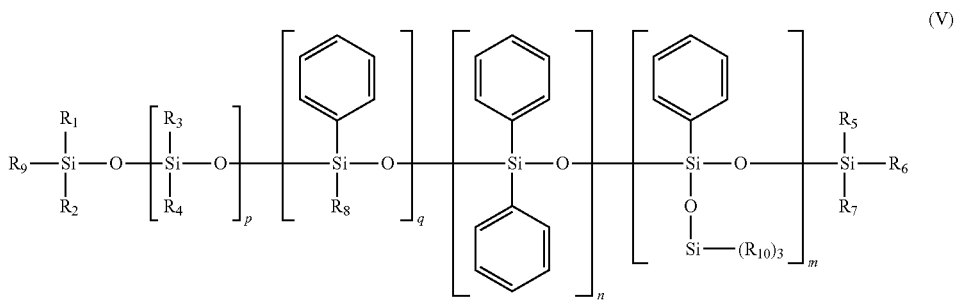

(V)

in which:

$R_1$ to $R_{10}$, independently of each other, are saturated or unsaturated, linear, cyclic or branched, preferably saturated or unsaturated, linear or branched, $C_1$-$C_{30}$ hydrocarbon-based radicals, m, n, p and q are, independently of each other, integers between 0 and 900, with the proviso that the sum m+n+q is other than 0.

Preferably, the sum m+n+q is between 1 and 100. Preferably, the sum m+n+p+q is between 1 and 900 and preferably between 1 and 800. Preferably, q is equal to 0.

Preferably, $R_1$ to $R_{10}$, independently of each other, represent a linear or branched $C_1$-$C_{30}$ alkyl radical, preferably $C_1$-$C_{20}$ and more particularly $C_1$-$C_{16}$ alkyl, or a monocyclic or polycyclic $C_6$-$C_{14}$ and in particular $C_{10}$-$C_{13}$ aryl radical, or an aralkyl radical, the alkyl part of which is preferably $C_1$-$C_3$ alkyl.

Preferably, $R_1$ to $R_{10}$ may each represent a methyl, ethyl, propyl, butyl, isopropyl, decyl, dodecyl or octadecyl radical, or alternatively a phenyl, tolyl, benzyl or phenethyl radical. $R_1$ to $R_{10}$ may in particular be identical, and in addition may be a methyl radical.

According to a first more particular embodiment of formula (V), mention may be made of:

i) phenyl silicone oils optionally bearing at least one dimethicone fragment corresponding to formula (VI) below, and mixtures thereof:

m, n and p are, independently of each other, integers between 0 and 100, with the proviso that the sum n+m is between 1 and 100.

Preferably, $R_1$ to $R_6$, independently of each other, represent a $C_1$-$C_{30}$, preferably $C_1$-$C_{20}$ and in particular $C_1$-$C_{16}$, alkyl radical, or a $C_6$-$C_{14}$ aryl radical which is monocyclic (preferably $C_6$) or polycyclic and in particular $C_{10}$-$C_{13}$, or an aralkyl radical (preferably the aryl part is $C_6$ aryl; the alkyl part is $C_1$-$C_3$ alkyl).

Preferably, $R_1$ to $R_6$ may each represent a methyl, ethyl, propyl, butyl, isopropyl, decyl, dodecyl or octadecyl radical, or alternatively a phenyl, tolyl, benzyl or phenethyl radical.

$R_1$ to $R_6$ may in particular be identical, and in addition may be a methyl radical. Preferably, m=1 or 2 or 3, and/or n=0 and/or p=0 or 1 can be applied, in formula (VI).

According to one particular embodiment, the non-volatile phenyl silicone oil is chosen from phenyl silicone oils bearing at least one dimethicone fragment.

Preferably, such oils correspond to compounds of formula (VI) in which:

A) m=0 and n and p are, independently of each other, integers between 1 and 100.

Preferably, $R_1$ to $R_6$ are methyl radicals.

According to this embodiment, the silicone oil is preferably chosen from a diphenyl dimethicone such as KF-54 from Shin Etsu, KF54HV from Shin Etsu, KF-50-300CS

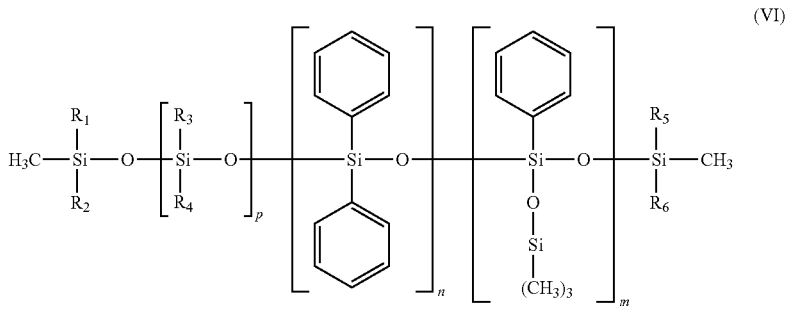

(VI)

in which:

$R_1$ to $R_6$, independently of each other, are saturated or unsaturated, linear, cyclic or branched, preferably saturated or unsaturated, linear or branched, $C_1$-$C_{30}$ hydrocarbon-based radicals, a preferably $C_6$-$C_{14}$ aryl radical or an aralkyl radical, the alkyl part of which is $C_1$-$C_3$ alkyl, from Shin Etsu, KF-53 from Shin Etsu or KF-50-100CS from Shin Etsu.

B) p is between 1 and 100, the sum n+m is between 1 and 100, and n=0.

These phenyl silicone oils optionally bearing at least one dimethicone fragment correspond more particularly to formula (VII) below:

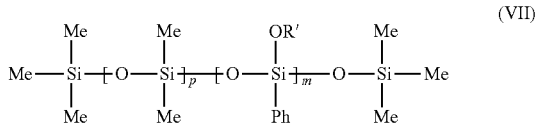

(VII)

in which Me is methyl and Ph is phenyl, OR' represents a group —OSiMe$_3$ and p is 0 or is between 1 and 1000, and m is between 1 and 1000. In particular, m and p are such that compound (VII) is a non-volatile oil.

According to a first embodiment of non-volatile phenyl silicone bearing at least one dimethicone fragment, p is between 1 and 1000 and m is more particularly such that compound (VII) is a non-volatile oil. Trimethylsiloxyphenyldimethicone, sold in particular under the reference Belsil PDM 1000 by the company Wacker, may, for example, be used.

According to a second embodiment of non-volatile phenylated silicone not bearing a dimethicone fragment, p is equal to 0 and m is between 1 and 1000, and in particular is such that the compound (VII) is a non-volatile oil.

Phenyltrimethylsiloxytrisiloxane, sold in particular under the reference Dow Corning 556 Cosmetic Grade Fluid (DC556), may, for example, be used.

ii) non-volatile phenyl silicone oils not bearing a dimethicone fragment corresponding to formula (VIII) below, and mixtures thereof:

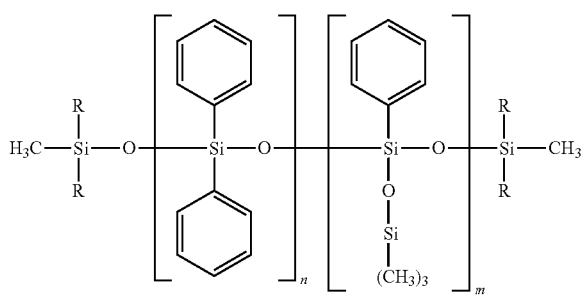

(VIII)

in which:
R, independently of each other, represent a saturated or unsaturated, linear, cyclic or branched, preferably saturated or unsaturated, linear or branched, $C_1$-$C_{30}$ hydrocarbon-based radical; more particularly, R represent a $C_1$-$C_{30}$ alkyl radical, an aryl radical, preferably a $C_6$-$C_{14}$ aryl radical, or an aralkyl radical, the alkyl part of which is $C_1$-$C_3$ alkyl,
m and n are, independently of each other, integers between 0 and 100, with the proviso that the sum n+m is between 1 and 100.

Preferably, R, independently of each other, represent a linear or branched $C_1$-$C_{30}$ and in particular a $C_1$-$C_{20}$, in particular $C_1$-$C_{16}$ alkyl radical, a monocyclic or polycyclic $C_6$-$C_{14}$, and in particular $C_{10}$-$C_{13}$, aryl radical, or an aralkyl radical of which preferably the aryl part is $C_6$ aryl and the alkyl part is $C_1$-$C_3$ alkyl.

Preferably, the groups R may each represent a methyl, ethyl, propyl, butyl, isopropyl, decyl, dodecyl or octadecyl radical, or alternatively a phenyl, tolyl, benzyl or phenethyl radical.

The groups R may in particular be identical, and in addition may be a methyl radical.

Preferably, m=1 or 2 or 3, and/or n=0 and/or p=0 or 1 can be applied, in formula (VIII).

According to one preferred embodiment, n is an integer between 0 and 100 and m is an integer between 1 and 100, with the proviso that the sum n+m is between 1 and 100, in formula (VIII). Preferably, R is a methyl radical.

According to one embodiment, a phenyl silicone oil of formula (VIII) with a viscosity at 25° C. of between 5 and 1500 mm$^2$/s (i.e. 5 to 1500 cSt), and preferably with a viscosity of between 5 and 1000 mm$^2$/s (i.e. 5 to 1000 cSt), may be used.

According to this embodiment, the non-volatile phenyl silicone oil is preferably chosen from phenyl trimethicones (when n=0) such as DC556 from Dow Corning (22.5 cSt), or else from diphenylsiloxyphenyl trimethicone oil (when m and n are between 1 and 100) such as KF56 A from Shin Etsu, or the Mirasil PTM oil from Bluestar Silicone (28 cSt). The values in parentheses represent the viscosities at 25° C.
e) phenyl silicone oils optionally bearing at least one dimethicone fragment corresponding to the following formula, and mixtures thereof:

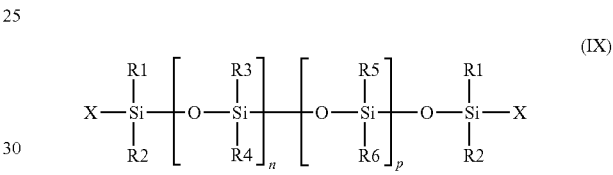

(IX)

in which:
$R_1$, $R_2$, $R_5$ and $R_6$, which may be identical or different, are an alkyl radical containing 1 to 6 carbon atoms,
$R_3$ and $R_4$, which may be identical or different, are an alkyl radical containing from 1 to 6 carbon atoms or an aryl radical (preferably $C_6$-$C_{14}$), with the proviso that at least one of $R_3$ and $R_4$ is a phenyl radical,
X is an alkyl radical containing from 1 to 6 carbon atoms, a hydroxyl radical or a vinyl radical,
n and p being an integer greater than or equal to 1, chosen so as to give the oil a weight-average molecular weight of less than 200 000 g/mol, preferably less than 150 000 g/mol and more preferably less than 100 000 g/mol.
f) and a mixture thereof.

If the composition comprises at least one second non-volatile silicone oil different from the first oil, said second oil is preferably chosen from non-volatile phenyl silicone oils optionally bearing a dimethicone fragment, for example the oils corresponding to those described in paragraph d), more particularly those of formula (VI) in i), preferably the silicones described in B) of formula (VII).

According to a particularly advantageous embodiment of the invention, the binder phase comprises at least one second oil different from the first oil.

In accordance with a particularly preferred embodiment of the invention, the binder phase comprises as second oil(s) at least one silicone or polar or apolar hydrocarbon-based non-volatile oil, and also mixtures thereof.

Among the apolar non-volatile hydrocarbon-based oils, hydrogenated or non-hydrogenated polybutenes, hydrogenated or non-hydrogenated polyisobutenes, hydrogenated or non-hydrogenated polydecenes, and also mixtures thereof, are particularly suitable for use, and preferably hydrogenated or non-hydrogenated polyisobutenes, and mixtures thereof.

Among the polar non-volatile hydrocarbon-based oils, ester oils and in particular hydroxylated or non-hydroxylated monoesters and diesters, comprising at least 18 carbon atoms in total, are particularly suitable for use.

Among the non-volatile silicone oils, it is preferred to use non-volatile phenyl silicone oils optionally bearing a dimethicone fragment, for example the oils described in paragraph d), more particularly those of formula (VI) in i), preferably the silicones described in B) of formula (VII).

Preferably, the binder phase comprises, as second oils, at least one non-volatile hydrocarbon-based oil and at least one non-volatile silicone oil.

Advantageously, the content of non-volatile hydrocarbon-based or non-volatile silicone second oil(s), or mixtures thereof, ranges from 5% to 40% by weight and preferably from 10% to 20% by weight relative to the weight of the composition.

Pasty Compound

The binder phase of the composition according to the invention also comprises at least one compound that is pasty at 25° C. and atmospheric pressure.

It should be noted that this pasty compound is water-immiscible.

For the purposes of the present invention, the term "pasty" means a compound that undergoes a reversible solid/liquid change of state, having anisotropic crystal organization in the solid state, and comprising, at a temperature of 23° C., a liquid fraction and a solid fraction.

In other words, the starting melting point of the pasty compound can be less than 23° C. The liquid fraction of the pasty compound, measured at 23° C., can represent from 9% to 97% by weight of the pasty compound. This liquid fraction at 23° C. preferably represents between 15% and 85% and more preferably between 40% and 85% by weight.

For the purposes of the invention, the melting point corresponds to the temperature of the most endothermic peak observed in thermal analysis (DSC) as described in the standard ISO 11357-3; 1999. The melting point of a pasty compound may be measured using a differential scanning calorimeter (DSC), for example the calorimeter sold under the name MDSC 2920 by the company TA Instruments.

The measuring protocol is as follows:

A sample of 5 mg of pasty compound placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of pasty fatty substance is measured as a function of the temperature. The melting point of the pasty compound is the temperature value corresponding to the top of the peak of the curve representing the variation in the difference in power absorbed as a function of the temperature.

The liquid fraction by weight of the pasty compound at 23° C. is equal to the ratio of the heat of fusion consumed at 23° C. to the heat of fusion of the pasty compound.

The heat of fusion of the pasty compound is the heat consumed by the compound in order to pass from the solid state to the liquid state. The pasty compound is said to be in the solid state when all of its mass is in crystalline solid form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instrument, with a temperature rise of 5° C. or 10° C. per minute, according to the standard ISO 11357-3; 1999.

The heat of fusion of the pasty compound is the amount of energy required to make the compound change from the solid state to the liquid state. It is expressed in J/g.

The heat of fusion consumed at 23° C. is the amount of energy absorbed by the sample to change from the solid state to the state that it has at 2° C., composed of a liquid fraction and a solid fraction.

The liquid fraction of the pasty compound measured at 32° C. preferably represents from 30% to 100% by weight of the pasty compound, preferably from 50% to 100% and more preferably from 60% to 100% by weight of the pasty compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same way as the heat of fusion consumed at 23° C.

The pasty compound may in particular be chosen from synthetic pasty compounds and fatty substances of plant origin.

The pasty compound(s) may be chosen in particular from:
  lanolin and derivatives thereof, such as lanolin alcohol, oxyethylenated lanolins, acetylated lanolin, lanolin esters such as isopropyl lanolate, and oxypropylenated lanolins,
  petroleum jelly (also known as petrolatum),
  polyol ethers chosen from $C_2$-$C_4$ polyalkylene glycol pentaerythrityl ethers, fatty alcohol ethers of sugars, and mixtures thereof. For example, mention may be made of polyethylene glycol pentaerythrityl ether comprising 5 oxyethylene units (5 OE) (CTFA name: PPG-5 Pentaerythrityl Ether), polypropylene glycol pentaerythrityl ether comprising five oxypropylene (5 OP) units (CTFA name: PPG-5 Pentaerythrityl Ether) and mixtures thereof, and more especially the mixture PEG-5 Pentaerythrityl Ether, PPG-5 Pentaerythrityl Ether and soybean oil, sold under the name Lanolide by the company Vevy, which is a mixture in which the constituents are in a 46/46/8 weight ratio: 46% PEG-5 Pentaerythrityl Ether, 46% PPG-5 Pentaerythrityl Ether and 8% soybean oil,
  polymeric or non-polymeric silicone compounds,
  polymeric or non-polymeric fluoro compounds,
  vinyl polymers, especially:
    olefin homopolymers and copolymers,
    hydrogenated diene homopolymers and copolymers,
    linear or branched oligomers, homopolymers or copolymers of alkyl (meth)acrylates preferably containing a $C_8$-$C_{30}$ alkyl group,
    oligomers, which are homopolymers and copolymers of vinyl esters containing $C_8$-$C_{30}$ alkyl groups, and
    oligomers, which are homopolymers and copolymers of vinyl ethers containing $C_8$-$C_{30}$ alkyl groups
  liposoluble polyethers resulting from the polyetherification between one or more $C_2$-$C_{100}$ and preferably $C_2$-$C_{50}$ diols.

Among the fat-soluble polyethers that are particularly considered are copolymers of ethylene oxide and/or of propylene oxide with long-chain $C_6$-$C_{30}$ alkylene oxides, more preferably such that the weight ratio of the ethylene oxide and/or propylene oxide to alkylene oxides in the copolymer is from 5:95 to 70:30. In this family, mention will be made especially of copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

esters and polyesters.

Among the esters, the following are especially considered:

- esters of a glycerol oligomer, especially diglycerol esters, in particular condensates of adipic acid and of diglycerol, for which some of the hydroxyl groups of the glycerols have reacted with a mixture of fatty acids such as stearic acid, capric acid, stearic acid, isostearic acid and 12-hydroxystearic acid, such as, for example, bis-diglyceryl polyacyladipate-2 sold under the reference Softisan® 649 by the company Sasol,
- vinyl ester homopolymers containing $C_8$-$C_{30}$ alkyl groups, such as polyvinyl laurate (sold especially under the reference Mexomer PP by the company Chimex),
- the arachidyl propionate sold under the brand name Waxenol 801 by Alzo,
- phytosterol esters,
- fatty acid triglycerides and derivatives thereof,
- pentaerythritol esters,
- esters of a diol dimer and of a diacid dimer, where appropriate esterified on their free alcohol or acid function(s) with acid or alcohol radicals, especially dimer dilinoleate esters; such esters may be chosen especially from the esters having the following INCI nomenclature: bis-behenyl/isostearyl/phytosteryl dimer dilinoleyl dimer dilinoleate (Plandool G), phytosteryl/isosteryl/cetyl/stearyl/behenyl dimer dilinoleate (Plandool H or Plandool S), and mixtures thereof,
- butters of plant origin, such as mango butter, such as the product sold under the name Lipex 203 by the company Aarhuskarlshamn, shea butter, in particular the product whose INCI name is Butyrospermum Parkii Butter, such as the product sold under the reference Sheasoft® by the company Aarhuskarlshamn, cupuacu butter (Rain Forest RF3410 from the company Beraca Sabara), murumuru butter (Rain Forest RF3710 from the company Beraca Sabara), cocoa butter; and also orange wax, for instance the product sold under the reference Orange Peel Wax by the company Koster Keunen,
- totally or partially hydrogenated plant oils, for instance hydrogenated soybean oil, hydrogenated coconut oil, hydrogenated rapeseed oil, mixtures of hydrogenated plant oils such as the mixture of hydrogenated soybean, coconut, palm and rapeseed plant oil, for example the mixture sold under the reference Akogel® by the company Aarhuskarlshamn (INCI name Hydrogenated Vegetable Oil), the trans-isomerized partially hydrogenated jojoba oil manufactured or sold by the company Desert Whale under the commercial reference Iso-Jojoba-50®, partially hydrogenated olive oil, for instance the compound sold under the reference Beurrolive by the company Soliance,
- hydrogenated castor oil esters, such as hydrogenated castor oil dimer dilinoleate, for example Risocast DA-L sold by Kokyu Alcohol Kogyo, and hydrogenated castor oil isostearate, for example Salacos HCIS (V-L) sold by Nisshin Oil, and mixtures thereof.

Preferably, the pasty compounds that are suitable for use in the invention are chosen from hydrocarbon-based compounds and comprise, besides carbon and hydrogen atoms, at least oxygen atoms. The pasty compounds therefore do not comprise any silicon atoms or any fluorine atoms.

According to a preferred embodiment, the binder phase comprises at least one pasty compound, advantageously chosen from lanolin and derivatives thereof, esters, or mixtures thereof. In particular, the pasty compound(s) are chosen from lanolin and derivatives thereof, esters of glycerol oligomers, butters of plant origin, totally or partially hydrogenated plant oils, and hydrogenated castor oil esters, or mixtures thereof.

As indicated above, the content of compound that is pasty at 25° C. and atmospheric pressure represents from 5% to 25% by weight and preferably from 5% to 15% by weight, relative to the composition.

Waxes

The composition according to the invention may optionally comprise at least one wax.

For the purposes of the present invention, the term "wax" means a lipophilic compound, which is solid at room temperature (25° C.), with a reversible solid/liquid change of state, which has a melting point of greater than or equal to 30° C. that may be up to 120° C.

The melting point of the wax may be measured using a differential scanning calorimeter (DSC), for example the calorimeter sold under the name DSC 30 by the company Mettler.

Preferably, the measuring protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The wax may especially have a hardness ranging from 0.05 MPa to 15 MPa and preferably ranging from 6 MPa to 15 MPa. The hardness is determined by measuring the compression force measured at 20° C. using a texturometer sold under the name TA-TX2i by the company Rheo, equipped with a stainless-steel cylinder 2 mm in diameter, travelling at a measuring speed of 0.1 mm/second, and penetrating the wax to a penetration depth of 0.3 mm.

The waxes may be hydrocarbon waxes or fluoro waxes, and may be of vegetable, mineral, animal and/or synthetic origin.

In particular, the waxes have a melting point of greater than 30° C. and better still greater than 45° C.

Apolar Wax

For the purposes of the present invention, the term "apolar wax" means a wax whose solubility parameter at 25° C. as defined below, $\delta_a$, is equal to 0 $(J/cm^3)^{1/2}$.

Apolar waxes are in particular hydrocarbon waxes composed solely of carbon and hydrogen atoms and devoid of heteroatoms, such as N, O, Si and P.

As illustrations of apolar waxes that are suitable for use in the invention, mention may be made especially of hydrocarbon-based waxes, for instance microcrystalline waxes, paraffin waxes, ozokerite, polyethylene waxes and microwaxes, especially polyethylene waxes.

Polar Wax

Within the meaning of the present invention, the term "polar wax" means a wax for which the solubility parameter $\delta_a$ at 25° C. is other than 0 $(J/cm^3)^{1/2}$.

In particular, the term "polar wax" means a wax whose chemical structure is formed essentially from, or even constituted of, carbon and hydrogen atoms, and comprising at least one highly electronegative heteroatom such as an oxygen, nitrogen, silicon or phosphorus atom.

The definition and calculation of the solubility parameters in the Hansen three-dimensional solubility space are described in the article by C. M. Hansen: *The three-dimensional solubility parameters*, J. Paint Technol. 39, 105 (1967).

According to this Hansen space:
- $\delta_D$ characterizes the London dispersion forces derived from the formation of dipoles induced during molecular impacts;
- $\delta_p$ characterizes the Debye interaction forces between permanent dipoles and also the Keesom interaction forces between induced dipoles and permanent dipoles;
- $\delta_h$ characterizes the specific interaction forces (such as hydrogen bonding, acid/base, donor/acceptor, etc.); and
- $\delta_a$ is determined by the equation: $\delta_a=(\delta_p^2+\delta_h^2)^{1/2}$.

The parameters $\delta_p$, $\delta_h$, $\delta_D$ and $\delta_a$ are expressed in $(J/cm^3)^{1/2}$.

The polar waxes may in particular be hydrocarbon-based, fluoro or silicone waxes.

Preferentially, the polar waxes may be hydrocarbon-based waxes or fluoro waxes.

The term "silicone wax" is intended to mean an oil comprising at least one silicon atom, and in particular comprising Si—O groups.

The term "hydrocarbon-based wax" means a wax formed essentially from, or even constituted of, carbon and hydrogen atoms, and optionally oxygen and nitrogen atoms, and that does not contain any silicon or fluorine atoms. It may contain alcohol, ester, ether, carboxylic acid, amine and/or amide groups.

According to a first preferred embodiment, the polar wax is a hydrocarbon-based wax.

As a hydrocarbon-based polar wax, a wax chosen from ester waxes and alcohol waxes is in particular preferred.

According to the invention, the term "ester wax" is intended to mean a wax comprising at least one ester function. The ester oils may also be hydroxylated.

According to the invention, the term "alcohol wax" means a wax comprising at least one alcohol function, i.e. comprising at least one free hydroxyl (OH) group.

The following may especially be used as ester wax:
ester waxes such as those chosen from:

i) waxes of formula $R_1COOR_2$ in which $R_1$ and $R_2$ represent linear, branched or cyclic aliphatic chains, the number of atoms of which varies from 10 to 50, which may contain a heteroatom such as O, N or P and the melting point of which varies from 25° C. to 120° C. In particular, use may be made, as an ester wax, of a $C_{20}$-$C_{40}$ alkyl (hydroxystearyloxy)stearate (the alkyl group comprising from 20 to 40 carbon atoms), alone or as a mixture, or a $C_{20}$-$C_{40}$ alkyl stearate. Such waxes are especially sold under the names Kester Wax K 82 P®, Hydroxypolyester K 82 P®, Kester Wax K 80 P® and Kester Wax K82H by the company Koster Keunen.

Use may also be made of a glycol and butylene glycol montanate (octacosanoate) such as the wax Licowax KPS Flakes (INCI name: glycol montanate) sold by the company Clariant.

ii) bis(1,1,1-trimethylolpropane) tetrastearate, sold under the name Hest 2T-45® by the company Heterene.

iii) dicarboxylic acid diester waxes of general formula $R^3$—(—OCO—$R^4$—COOR—$R^5$), in which $R^3$ and $R^5$ are identical or different, preferably identical and represent a $C_4$-$C_{30}$ alkyl group (alkyl group comprising from 4 to 30 carbon atoms) and $R^4$ represents a linear or branched $C_4$-$C_{30}$ aliphatic group (alkyl group comprising from 4 to 30 carbon atoms) which may or may not contain one or more unsaturated groups. Preferably, the $C_4$-$C_{30}$ aliphatic group is linear and unsaturated.

iv) Mention may also be made of the waxes obtained by catalytic hydrogenation of animal or vegetable oils having linear or branched $C_8$-$C_{32}$ fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol, such as those sold under the names Phytowax Ricin 16L64® and 22L73® by the company Sophim. Such waxes are described in patent application FR-A-2 792 190. Mention may be made, as waxes obtained by hydrogenation of olive oil esterified with stearyl alcohol, of those sold under the name Phytowax Olive 18 L 57.

v) Mention may also be made of beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumach wax, montan wax, orange wax, laurel wax and hydrogenated jojoba wax.

According to a preferred embodiment, a composition in accordance with the invention comprises candelilla wax.

According to another embodiment, the polar wax may be an alcohol wax.

Alcohol waxes that may be mentioned include for example the wax Performacol 550-L Alcohol from New Phase Technologies, stearyl alcohol and cetyl alcohol.

According to a second embodiment, the polar wax may be a silicone wax, for instance siliconized beeswax.

Preferably, in the composition according to the invention, if it comprises a wax, whether it is a polar or apolar wax, their content does not exceed 5% by weight (i.e. between 0 and 5% by weight) and even more particularly does not exceed 2% by weight (i.e. between 0 and 2% by weight), relative to the total weight of the composition.

Volatile Oils

The composition according to the invention may optionally comprise at least one volatile oil, in particular a hydrocarbon-based or silicone oil.

For the purposes of the present invention, the term "volatile oil" means an oil whose flash point is strictly less than 49° C. The flash point is measured in a closed cup using a Pensky-Martens machine.

The volatile hydrocarbon-based oils may be chosen from hydrocarbon-based oils containing from 8 to less than 16 carbon atoms, and especially branched $C_8$-$C_{16}$ alkanes (also known as isoparaffins), for instance isododecane (also known as 2,2,4,4,6-pentamethylheptane), isodecane and, for example, the oils sold under the trade names Isopar® or Permethyl®. Among the volatile oils, mention may also be made of fragrances.

Volatile oils that may also be used include volatile silicone oils, for instance volatile linear or cyclic silicone oils, especially those with a viscosity ≤8 centistokes ($8 \times 10^{-6}$ m$^2$/s) and especially containing from 2 to 10 silicon atoms, and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with a viscosity of less than or equal to 6 cSt, heptamethylhexyltrisiloxane, heptamethyloctyltrisiloxane, hexamethyldisiloxane, octamethyltrisiloxane and decamethyltetrasiloxane, and mixtures thereof.

Volatile fluoro oils such as nonafluoromethoxybutane or perfluoromethylcyclopentane, and mixtures thereof, may also be used.

Preferably, in the composition according to the invention, if it comprises one or more volatile oils, their content does not exceed 10% by weight (i.e. between 0 and 10% by weight) and preferably does not exceed 5% by weight (i.e. between 0 and 5% by weight), relative to the total weight of the composition.

Usual Additional Cosmetic Ingredients

A composition according to the invention may also comprise any usual cosmetic ingredient, which may be chosen especially from antioxidants, fragrances, preserving agents, neutralizers, surfactants, sunscreens, sweeteners, vitamins, moisturizers, emollients, hydrophilic or lipophilic active agents, free-radical scavengers and sequestrants, and mixtures thereof.

The composition according to the invention may also comprise at least one film-forming polymer chosen from vinyl polymers comprising at least one carbosiloxane dendrimer-based unit; film-forming block ethylenic copolymers; alkylcelluloses; silicone resins, silicone polyamides, or mixtures thereof.

Needless to say, a person skilled in the art will take care to select the optional additional ingredients and/or the amount thereof such that the advantageous properties of the composition according to the invention are not, or are not substantially, adversely affected by the envisaged addition.

It should be noted that, depending on its liquid or solid state, the ingredient added is introduced with the pulverulent phase or with the binder phase.

Preparation of the Composition

The compositions according to the invention may be prepared according to the following protocol.

The materials forming the pulverulent phase are introduced directly into a kneader-mixer usually used for pasty and/or powdery products, such as Baker-Perkins turbine mixers/granulators, dough mixers or continuous twin-screw kneaders of the BC21 or BC45 kneader-extruder type from the company Clextral, following in particular the suppliers' instructions.

The crosslinked elastomeric organopolysiloxane conveyed with at least a first oil is introduced with the binder phase into the pulverulent phase, or separately from the binder phase.

The binder phase comprises the non-volatile oil(s), at least one pasty compound, optionally at least one wax and optionally at least one volatile oil.

The binder phase and the organopolysiloxane conveyed in at least a first non-volatile oil are introduced with stirring.

The temperature at which the composition is prepared usually ranges between 20° C. and 45° C.

The composition, whether it is in pulverulent or pasty form, may be weighed out in a suitable crucible or container, and then subjected to pressing, for example on a Vetraco machine.

Treatment Process Using the Composition

The compositions according to the invention may be applied using a finger or advantageously using a specific foam applicator or a specific sponge, suitable for handling such a composition, to keratin materials, in particular the skin and the lips, or alternatively using a squeeze-pen.

In the examples that follow, the weight percentages are indicated relative to the total weight of the composition.

The weight percentages are indicated as weight of starting material.

EXAMPLE 1

The composition is prepared from the ingredients (amounts expressed as weight percentages of starting material):

| Phase | Ingredient | Amount |
|---|---|---|
| D | Pentaerythrityl tetrakis(di-t-butyl)hydroxyhydrocinnamate | 0.03 |
| A | Perlite | 4 |
| B | Blue 1 Lake | 0.22 |
| B | Red 7 | 2.9 |
| B | Titanium dioxide | 1.7 |
| B | Red 28 Lake | 3.25 |
| D | Bis(diglyceryl) poly(2-acyladipate) (Softisan 649 from Sasol) | 12.68 |
| D | Diisostearyl malate | 5.76 |
| D | Isostearyl isostearate | 2.45 |
| B | Mica/lauroyllysine | 2.67 |
| A | Mica | qs |
| D | Hydrogenated polyisobutene (Parleam from NOF) | 5.38 |
| A | HDI/trimethylol hexyllactone crosspolymer (Plastic Powder D400 from Toshiki Pigment) | 3.67 |
| D | Phenyl trimethicone (Dow Corning ® 556 Cosmetic Grade Fluid from Dow Corning) | 3.69 |
| D | Dimethicone and dimethicone crosspolymer (Dow Corning 9041 Silicone Elastomer Blend from Dow Corring) | 29.5 |
| D | Caprylyl glycol | 0.5 |

Phases A and B are introduced into a Baker mixer and mixed for 3 minutes 30 seconds (paddle speed of 3000 rpm/motor speed of 2700 rpm).

A mixture C is obtained, which is transferred into a kneader.

A homogeneous mixture of the ingredients of phase D is prepared at 25° C. and added portionwise to mixture C, with gentle stirring, until the composition is fully homogenized.

A homogeneous, cohesive paste is obtained, which is packaged in a dish. It is supple on taking up and on application.

The deposit is thin, matt and comfortable. Furthermore, it has good persistence.

EXAMPLES 2

The compositions whose ingredients are listed in the table below are prepared (amounts expressed as weight percentages of starting material, unless otherwise mentioned):

| Phase | Ingredients | Composition 1 invention | Composition 2 comparative |
|---|---|---|---|
| D | Pentaerythrityl tetra-di-t-butyl hydroxyhydrocinnamate (Tinogard TT, BASF) | 0.02 | 0.02 |

-continued

| Phase | Ingredients | Composition 1 invention | Composition 2 comparative |
|---|---|---|---|
| A | Talc | 3.34 | 3.342 |
| B | Titanium dioxide | 4.55 | 4.55 |
| B | Yellow 6 lake | 4 | 4 |
| B | Red 28 lake | 2.5 | 2.5 |
| B | Iron oxides | 0.14 | 0.14 |
| D | Bis-diglyceryl polyacyladipate-2 (Softisan 649, Cremer Oleo) | 10.53 | 8.41 |
| D | Diisostearyl malate | 4.79 | 3.82 |
| D | Isostearyl isostearate | 2.03 | 1.62 |
| B | Mica/lauroyllysine | 2.67 | 2.67 |
| B | Mica | 19.14 | 19.14 |
| D | Fragrance | 0.1 | 0.1 |
| D | Hydrogenated polyisobutene (Parleam from NOF) | 4.47 | 3.57 |
| D | Polyethylene (Asensa SC 211, Honeywell) | 1.1 | 3.85 |
| D | Polyethylene (Performalene 500-L Polyethylene, New Phase Technologies) | 0.9 | 3.15 |
| B | HDI/trimethylol hexyl lactone crosspolymer (Plastic Powder D400 from Toshiki Pigment) | 3.67 | 3.67 |
| D | Phenyl trimethicone (Dow Corning ® 556 Cosmetic Grade Fluid from Dow Corning) | 3.06 | 2.45 |
| B | Vinyl dimethicone/methicone silsesquioxane crosspolymer (KSP100 from Shin-Etsu) | 2 | 2 |
| D | Dimethicone (and) dimethicone crosspolymer (Dow Corning 9041 Silicone Elastomer Blend; Dow Corning) | 29 | 29 |
| D | Ethylhexyl glycerol | 0.5 | 0.5 |
| D | Pentylene glycol | 1 | 1 |
| D | Caprylyl glycol | 0.5 | 0.5 |

Phases A and B are introduced into a Baker mixer and mixed for 3 minutes 30 seconds (paddle speed of 3000 rpm/motor speed of 2700 rpm).

A mixture C is obtained, which is transferred into a kneader.

A homogeneous mixture of the ingredients of phase D is prepared by heating until complete homogenization of phase D and added portionwise to mixture C, with gentle stirring, until the composition is fully homogenized.

The composition is then packaged in a dish.

In the case of composition 1 according to the invention, comprising 2% by weight of wax, a paste is obtained that is homogeneous, stable, without exudation of oil, supple and cohesive. It is easy to take up, and easy and pleasant to apply.

A thin, homogeneous, covering and matt deposit that is very comfortable is obtained. It also shows good persistence of the colour and of the matt effect.

In the case of the comparative composition 2 comprising a wax content of 7% by weight, the composition obtained is not in the form of a paste, it is very hard and is very difficult to take up.

The invention claimed is:

1. A process for preparing an anhydrous composition in powder form or in paste form, the process comprising:
    preparing from 30% to 65% by weight, relative to the weight of the composition, of organic, mineral or composite solid particles, or any mixture thereof;
    preparing 10% to 40% by weight, relative to the weight of the composition, of a mixture comprising at least one organopolysiloxane elastomer conveyed in at least a first silicone or hydrocarbon-based non-volatile oil;
    preparing 10%0 to 45% by weight, relative to the weight of the composition, of an organic binder phase comprising at least a second hydrocarbon-based or silicone non-volatile oil, identical to or different from the first oil, at least one pasty compound having a content of between 5% and 25% by weight, relative to the weight of the composition, optionally at least one wax and optionally at least one volatile oil, the wax content not exceeding 5% by weight, relative to the weight of the composition;
    introducing the binder phase and said conveyed organopolysiloxane elastomer into the solid particles with stirring, wherein the conveyed organopolysiloxane elastomer is introduced with the binder phase or separately therefrom.

2. The process according to claim 1, wherein the organopolysiloxane elastomer conveyed in at least a first oil is non-emulsifying.

3. The process according to claim 1, wherein the organopolysiloxane elastomer conveyed in at least a first oil is obtained by crosslinking addition reaction (A) of diorganopolysiloxane containing at least two hydrogens each bonded to a silicon, and (B) of diorganopolysiloxane containing at least two ethylenically unsaturated groups bonded to silicon, optionally in the presence of a platinum catalyst (C).

4. The process according to claim 1, wherein the content of mixture of organopolysiloxane elastomer(s) conveyed in at least a first non-volatile oil represents from 15% to 35% by weight relative to the weight of the composition.

5. The process according to claim 1, wherein the organopolysiloxane elastomer content in said mixture is such that the organopolysiloxane elastomer content in the composition, expressed as organopolysiloxane elastomer, ranges from 2% to 100/% by weight of the composition.

6. The process according to claim 1, wherein the solid particle(s) are chosen from coloured solid particles, nacres, organic, mineral or mixed fillers, and mixtures thereof.

7. The process according to claim 6, wherein the content of coloured particle(s) represents from 5% to 25% by weight, relative to the weight of the composition.

8. The process according to claim 7, wherein the organic, mineral or mixed filler(s) are chosen from talc; mica; fumed or non-fumed silica, which has optionally undergone a hydrophilic or hydrophobic treatment; perlite; kaolin; bentonite; starch; boron nitride; hollow polymer microspheres; silicone resin microbeads; precipitated calcium carbonate; magnesium carbonate, magnesium hydrocarbonate; hydroxyapatite; hollow silica microspheres; polyorganosiloxane elastomer particles; polyurethane particles; polyamide, polyethylene or polymethyl methacrylate powders, polytetrafluoroethylene powders, acrylic acid copolymer powders, lauroyllysine, hollow polymer microspheres, silicone resin microbeads, synthetic or natural micronized waxes, metal soaps derived from organic carboxylic acids containing from 8 to 22 carbon atoms; glass or ceramic microcapsules; or mixtures thereof.

9. The process according to claim 7, wherein the content of organic, mineral or composite filler(s), or mixtures thereof, represents from 10% to 40% by weight, relative to the weight of the composition.

10. The process according to claim 1, wherein at least a first oil and/or at least a second oil is chosen from polar or apolar non-volatile hydrocarbon-based oils, or mixtures thereof.

11. The process according to claim 10, wherein the apolar non-volatile hydrocarbon-based oil(s) are chosen from liquid paraffin, squalane, isohexadecane, isoeicosane, naphthalene oil, hydrogenated or non-hydrogenated polybutenes, hydrogenated or non-hydrogenated polyisobutenes, decene/butene copolymers, polybutene/polyisobutene copolymers, hydrogenated or non-hydrogenated polydecenes, and mixtures thereof.

12. The process according to claim 10, wherein the polar non-volatile hydrocarbon-based oil(s) are chosen from $C_{10}$-$C_{26}$ alcohols; ester oils; hydrocarbon-based plant oils; vinylpyrrolidone/I-hexadecene copolymers; $C_{12}$-$C_{26}$ fatty acids; dialkyl carbonates; and mixtures thereof.

13. The process according to claim 1, wherein at least a first oil and/or at least a second oil is chosen from non-phenyl non-volatile silicone oils, from phenyl silicone oils optionally bearing a dimethicone fragment, or mixtures thereof.

14. The process according to claim 1, wherein the binder phase comprises, as second oils, different from the first oil, at least one non-volatile hydrocarbon-based oil, and at least one non-volatile silicone oil.

15. The process according to claim 1, wherein the content of non-volatile hydrocarbon-based compound(s), of non-volatile silicone compound(s), or mixtures thereof, ranges from 5% to 40% by weight, relative to the weight of the composition.

16. The process according to claim 1, wherein the first oil(s) are chosen from non-phenyl non-volatile silicone oils, from phenyl silicone oils optionally bearing a dimethicone fragment, or mixtures thereof.

17. The process according to claim 1, wherein the binder phase comprises at least one hydrocarbon-based or silicone compound that is pasty at 25° C. and atmospheric pressure, chosen from:
lanolin,
polymeric or non-polymeric silicone compounds,
polymeric or non-polymeric fluoro compounds,
vinyl polymers, olefin copolymers, or hydrogenated diene homopolymers and copolymers,
linear or branched oligomers, homopolymers or copolymers of alkyl (meth)acrylates,
oligomers, homopolymers and copolymers of vinyl esters containing $C_8$-$C_{30}$ alkyl groups,
oligomers, homopolymers and copolymers of vinyl ethers containing $C_8$-$C_{30}$ alkyl groups,
liposoluble polyethers resulting from the polyetherification between one or more $C_2$-$C_{100}$ diols,
esters and polyesters,
and mixtures thereof.

18. The process according to claim 1, wherein the content of compound(s) that are pasty at 25° C. and atmospheric pressure represents from 5% to 15% by weight, relative to the composition.

19. The process according to claim 1, wherein the composition comprises at least one hydrocarbon-based or silicone volatile oil, in a content not exceeding 10% by weight, relative to the weight of the composition.

20. A process for making up and/or caring for the lips, comprising applying the composition obtained by the process according to claim 1 to the lips.

* * * * *